United States Patent
Ouji et al.

(10) Patent No.: US 9,984,458 B2
(45) Date of Patent: May 29, 2018

(54) VESSEL SEGMENTATION METHOD

(71) Applicant: Agfa HealthCare NV, Mortsel (BE)

(72) Inventors: Asma Ouji, Mortsel (BE); Yoni De Witte, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 96 days.

(21) Appl. No.: 15/030,096

(22) PCT Filed: Oct. 28, 2014

(86) PCT No.: PCT/EP2014/073067
§ 371 (c)(1),
(2) Date: Apr. 18, 2016

(87) PCT Pub. No.: WO2015/063054
PCT Pub. Date: May 7, 2015

(65) Prior Publication Data
US 2016/0260212 A1    Sep. 8, 2016

(30) Foreign Application Priority Data

Oct. 30, 2013 (EP) .................................. 13190817

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/461* (2013.01); *A61B 6/504* (2013.01); *A61B 6/5211* (2013.01); *G06T 7/11* (2017.01); *G06T 7/155* (2017.01); *G06T 7/187* (2017.01); *G06T 7/20* (2013.01); *G06T 7/60* (2013.01); *G06T 2207/20012* (2013.01); *G06T 2207/20101* (2013.01); *G06T 2207/20156* (2013.01); *G06T 2207/30101* (2013.01)

(58) Field of Classification Search
CPC ......... G06T 7/0012; G06T 7/187; G06T 7/11; G06T 7/155; G06T 7/20; G06T 7/60; G06T 2207/20012; G06T 2207/20156; G06T 2207/30101; G06T 2207/20101; A61B 6/032; A61B 6/461; A61B 6/504; A61B 6/5211
See application file for complete search history.

(56) References Cited

U.S. PATENT DOCUMENTS

2003/0223627 A1* 12/2003 Yoshida ................ G06T 7/0012
                                                            382/128
2005/0157925 A1*  7/2005 Lorenz ..................... G06T 7/11
                                                            382/173
(Continued)

OTHER PUBLICATIONS

Kirbas et al. "A Review of Vessel Extraction Techniques and Algorithms", XP007900870, Jan. 2003, 52 pages, URL: http://www.siue.edu/~sumbaug/RetinalProjectPapers/Review%20of%20Blood%20Vessel%20Extraction%20Teohniques%20and%20Algorithms.pdf.

(Continued)

*Primary Examiner* — Jon Chang
(74) *Attorney, Agent, or Firm* — Keating & Bennett, LLP

(57) ABSTRACT

Vascular structures are segmented by a locally adaptive method based on iterative region growing and morphological operations.

4 Claims, 1 Drawing Sheet

(51) Int. Cl.
*A61B 6/03* (2006.01)
*G06T 7/20* (2017.01)
*G06T 7/60* (2017.01)
*G06T 7/11* (2017.01)
*G06T 7/155* (2017.01)
*G06T 7/187* (2017.01)

(56) References Cited

U.S. PATENT DOCUMENTS

| | | | |
|---|---|---|---|
| 2007/0031019 A1* | 2/2007 | Lesage | G06T 7/60 |
| | | | 382/131 |
| 2007/0047792 A1 | 3/2007 | Scheuering et al. | |
| 2007/0103464 A1* | 5/2007 | Kaufman | G06T 7/0012 |
| | | | 345/424 |
| 2010/0296709 A1 | 11/2010 | Ostrovsky-Berman et al. | |

OTHER PUBLICATIONS

Official Communication issued in International Patent Application No. PCT/EP2014/073067, dated Feb. 2, 2015.

\* cited by examiner

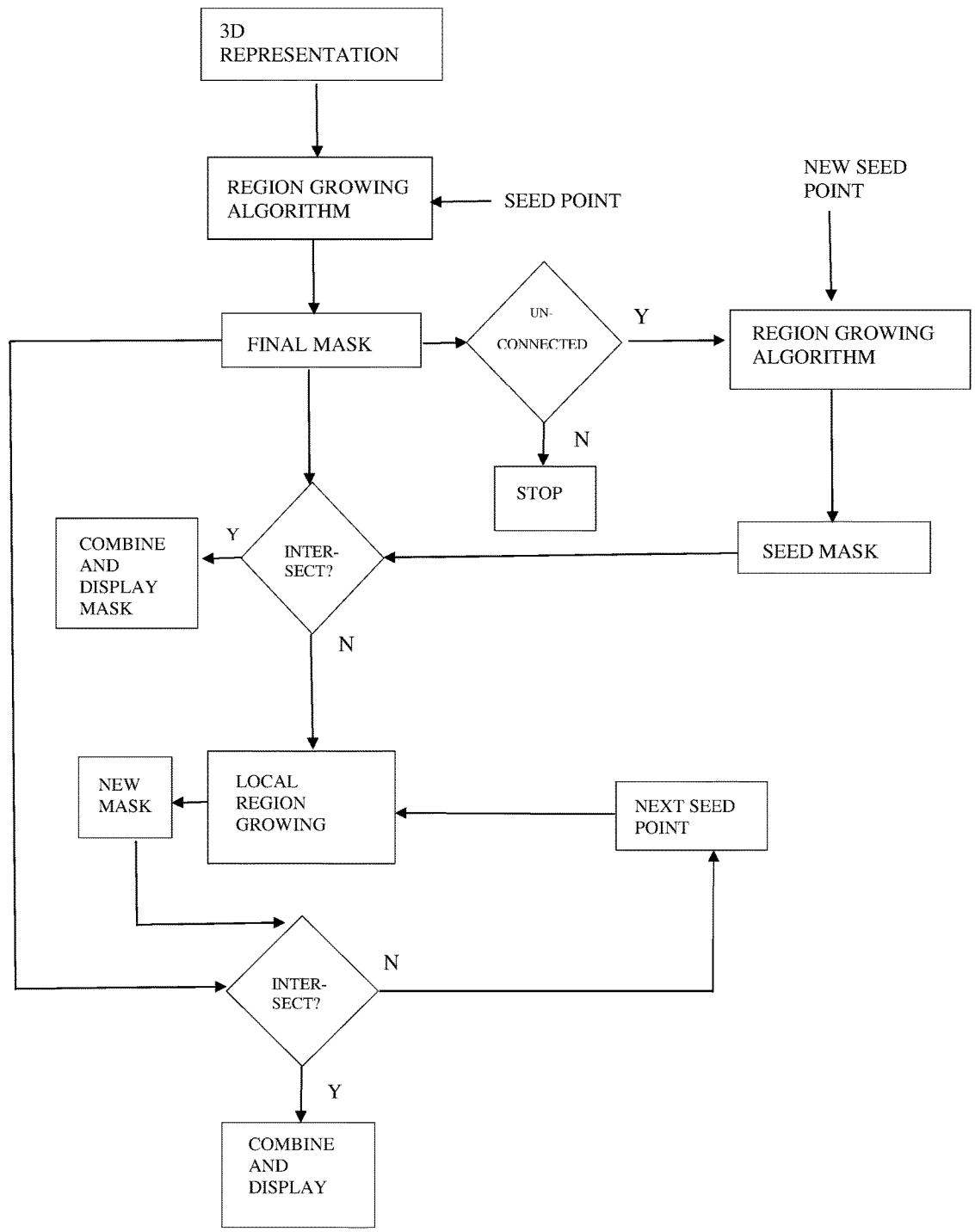

VESSEL SEGMENTATION METHOD

CROSS-REFERENCE TO RELATED APPLICATIONS

This application is a 371 National Stage Application of PCT/EP2014/073067, filed Oct. 28, 2014. This application claims the benefit of European Application No. 13190817.0, filed Oct. 30, 2013, which is incorporated by reference herein in its entirety.

BACKGROUND OF THE INVENTION

1. Field of the Invention

The present invention relates to a method for segmentation of a structure, more particularly segmentation of a vessel structure in a 3D medical image reconstruction.

2. Description of the Related Art 3D reconstructions of MRA (magnetic resonance angiography) and CTA (X-ray CT angiography), in which vessels are enhanced to have higher intensity values, are widely used for the diagnosis of serious circulation diseases.

In such studies, the segmentation of vascular structures is particularly valuable for diagnosis assistance, treatment and surgery planning. Indeed, it is a fundamental step for the accurate visualization of vessels from complex datasets and for the quantification of pathologies.

It is also a valuable input for advanced vessel tracking applications.

Vascular segmentation is an especially specific and challenging problem. Besides acquisition-dependent considerations about contrast, resolution, noise and artifacts, vascular networks can be particularly complex structures. Blood vessels potentially exhibit high variability of size and curvature. Their appearance and geometry can be perturbed by stents, calcifications, aneurysms, and stenoses. Furthermore, they are often embedded in complex anatomical scenes, surrounded by other organs, mainly bones which have a similar density, in an angiographic setting.

In addition to the above general considerations, more specific image properties, such as the pixel intensity variations related to the local amount of blood flow and the partial volume effects, make the vessel segmentation a difficult task. The partial volume effects mainly affect thin vessels reducing the intensity of vessel parts as the low pass filtering effect. So the range of the intensity of the blood vessel is not restricted in a small interval but spread widely.

For all these reasons, the generic region growing, as well as thresholding, is not appropriate to extract the whole part of the vessels: it usually results in false detection problems. To get correct segmentation results by region growing, it is necessary to rely on flexibly adapted approaches according to the local characteristics in each region.

Similar problems may be encountered when segmenting other structures such as bone structures.

It is an aspect of the present invention to provide a segmentation method that overcomes the described disadvantages of prior art methods.

SUMMARY OF THE INVENTION

The above-mentioned aspects are realised by a method having the specific steps set out below.

According to a preferred embodiment of the invention a locally adaptive method based on iterative region growing and morphological operations is proposed in order to segment structures such as vascular structures in CTA images.

The method was designed to segment peripheral vessels. However, it may be applied to other structures such as bones. Its extension to other structure segmentation may require an adaptation of the threshold values.

Specific features for preferred embodiments of the invention are set out below.

A preferred embodiment of the present invention is generally implemented in the form of a computer program product adapted to carry out the method steps when run on a computer combined with user interaction to define some of the required seed points. The computer program product is commonly stored in a computer readable carrier medium such as a DVD. Alternatively the computer program product takes the form of an electric signal and can be communicated to a user through electronic communication.

The method can be implemented in a workstation coupled to an image acquisition device or to a picture archiving and communication system or the like.

Further advantages and preferred embodiments of the present invention will become apparent from the following description.

BRIEF DESCRIPTION OF THE DRAWING

The FIGURE shows a flowchart including steps of segmenting an anatomical structure in a 3D medical image according to a preferred embodiment of the present invention.

DETAILED DESCRIPTION OF THE PREFERRED EMBODIMENTS

In order to execute a preferred embodiment of the method of the present invention, the user performs a number of actions on the display of a 3D volume (or on the display of slice image), as shown in the FIGURE.

An image processing device runs a software implementation of the method as explained further on.

First the user places a seed point on a displayed 3D volume or on a displayed slice image.

The coordinates of the seed point are used by the software implementation of the segmentation steps in the method of the present invention.

The segmentation mask resulting from application of the segmentation algorithm is displayed.

The user examines the displayed segmentation mask and if he wants to extend the segmentation mask (this is in case there is a missing region in the result of the first segmentation operation), he places a second seed point. This second seed point is placed in the missing region.

The segmentation operation is again performed and results in a second mask which is displayed.

The last two steps are repeated until the user stops placing additional seed points.

On most datasets placing one seed point is enough to segment the complete vessel tree. Specific situations such as volumes with thin vessels and/or occlusions may require additional seed points to be placed.

The output of the method is a segmentation mask which can be displayed. The segmentation mask is a 3D binary mask where a voxel that has been has been classified as belonging to the vessel is marked, e.g. by firing the displayed voxel.

The mask must be connected. This means that it has to be composed of only one connected component.

Lower and upper thresholds are associated to each mask created within any step of this algorithm. They correspond to the minimum and maximum voxel intensity within that mask.

A preferred embodiment of an algorithm for performing the segmentation is described below.

Let Mask_final be the final vessel segmentation mask. Mask_final is initially empty.

For each new seed point S placed by the user, the following steps are executed:

1. Apply a basic region growing algorithm starting from the point S. A region growing algorithm requires the input of a lower and upper threshold of the growing. The lower and upper thresholds of the growing are determined based on the gray value of S. The output of the growing is a segmentation mask called Mask_S.

2. If S is the first seed point placed by the user then Mask_final is given by Mask_S (Mask_final←Mask_S) and the algorithm ends.

3. Else, if Mask_S intersects Mask_final (if Mask_S ∩Mask_final≠φ) then Mask_final is replaced by the union of Mask_final and Mask_S (Mask_final←Mask_S ∪Mask_final) and the algorithm ends.

4. Otherwise, a locally adaptative region growing is applied with as input the seed point S and the previous mask Mask_final.

Each step from the above algorithm is detailed in the following sections.

Basic Region Growing From One Seed Point

Every time the user places a seed point, a basic region growing method is applied as a first step.

For its operation the basic region growing algorithm needs the input of one seed point. This algorithm works as follows:

1. The corresponding voxel to the placed seed point is identified (S).

2. If the lower and upper thresholds are not defined as input, these values are determined based on 80% and 110% of the Hounsfield unit value at the voxel S.

3. Voxels which are within the range defined by the lower and upper threshold values yield an intermediate binary mask.

4. Voxels in the intermediate mask that are connected to the seed point (voxel S) yield a binary mask (Mask_S). This mask is the output of the basic region growing operation. A voxel is connected to S if the two voxels are included in the same 'connected component'. A connected component is defined as a group of voxels in which each voxel is adjacent to at least one of the other voxels in that connected component. Adjacency is in this preferred embodiment defined in the 6-neighborhood sense.

Locally Flexible Region Growing with Multiple Seed Points

If the user places only one seed point, the algorithm stops after the basic region growing step.

If the user places a second (or third, fourth, etc.) seed point, the basic region growing algorithm is run again with the latter seed point as input. It yields a new segmentation mask (Mask_S). The intersection between this mask and the existing mask (yield by the previous seed points) is computed.

If the intersection is not empty, the final mask is obtained by the union of these two masks.

Otherwise, a locally adaptative region growing algorithm is applied to cope well with the intensity variation in 3-D space. This algorithm is based on running the region growing algorithm iteratively with the input of automatically defined seed points and thresholds each time. This algorithm prevents over-growth by controlling the threshold rage evolution. This algorithm is detailed below.

Algorithm

Let Mask_final be the previously computed mask.

Initially, the basic region growing is run on the last placed seed point and yields the mask Mask_S. Let lower_threshold and upper_threshold the initial lower and upper thresholds associated to Mask_S.

While Mask_S does not intersect Mask_final the following steps are repeated.

1. Find the next seed point. This step requires the current Mask_S as well as its associated thresholds and the previous mask Mask_final as input. This seed point lookup algorithm is defined in the following section. Let S be the output seed point.

2. Estimate distance1: the gray value distance between S and lower_threshold.

3. Estimate distance2: the gray value distance between S and upper_threshold.

4. Consider distance: the minimum between distance1 and distance2.

5. If distance is lower than a predefined threshold (in one preferred embodiment this value is set to 20 HU based on experiments) then the threshold range is enlarged so that S fits into it; i.e. lower_threshold is replaced by the minimum of lower_threshold and the gray value of S, and upper_threshold is replaced by the maximum of upper_threshold and the gray value of S. Otherwise (if distance is higher than the predefined threshold), S is replaced by a new seed point and a jump to step 2 is performed. The seed point replacement algorithm is defined in the following sections. It runs with the same input as the seed point lookup algorithm. This step insures that the growing is progressing without exploding the threshold range. Indeed, if the threshold range becomes too wide, the vessel segmentation mask would probably over-grow up.

6. Mask_S is replaced by the union of Mask_S and the output yield by running a basic region growing with the seed point S and the thresholds lower_threshold and upper_threshold as inputs.

7. Check that Mask_S has not grown too much. The verification is performed by comparing the number of voxels within Mask_S in the current iteration and the previous one. If the growth exceeds a factor of 5 (this factor value has been fixed based on experiments on different datasets) then an overgrowth is detected so the algorithm stops.

At the end of the above loop a segmentation mask (Mask_S) is created. This mask is the final one (Mask_final←Mask_S).

Seed Point Lookup Algorithm

Each iteration of the locally adaptative region growing algorithm requires the determination of a new seed point and lower and upper thresholds depending on that seed point.

The computation of the new seed point requires the input of the last region growing mask Mask_S, its associated thresholds lower_threshold and upper_threshold and the previous mask Mask_final.

The new seed point S is determined based on the following considerations:

S is outside the mask Mask_S in order to extend it.

The gray value of S should be as close as possible to one of the thresholds lower_threshold and upper_threshold. This condition is used to prevent over-growth.

S must be adjacent to Mask_S.

S must be as close as possible to the previous mask Mask_final.

The above constraints insure to grow the mask Mask_S in the appropriate direction so as to intersect Mask_final. They also intend to prevent over-growth by limiting the lookup area.

The seed point look up algorithm is defined below.

Algorithm

1. Find in the 3D volume the slice fulfilling the conditions of being the closest to Mask_final in one hand and including adjacent voxels to Mask_S in the other hand. It must be that this slice does not intersect Mask_S. A slice is an image defined as a 2D projection of the 3D volume along the vertical axis. Let the found slice be called Slice_Adjacent.

2. Extract Mask_Adjacent which is a 2D binary mask corresponding to the adjacent voxels to Mask_S that are included in Slice_Adjacent.

3. In Mask_Adjacent, find the voxel S1 having the closest gray value to lower_threshold. Let distance1 be the gray value distance between S1 and lower_threshold.

4. In Mask_Adjacent, find the voxel S2 having the closest gray value to upper_threshold. Let distance2 be the gray value distance between S2 and upper_threshold.

5. The final seed point S (the output of the current algorithm) is S1 if distance1 is lower than distance2 and S2 otherwise.

Seed Point Replacement Algorithm

In some cases, mainly when the vessel includes high curvature zones, the seed point determined using the above algorithm may lead to an over-growth (because its gray value is too distant from the lower and upper thresholds). In order to prevent such cases, that seed point is replaced as soon as it is suspected.

The seed point replacement algorithm is similar to the previous algorithm determining the seed point S. The only difference between them is that the seed point is not searched within the adjacency area but its close neighbourhood. Thus the new seed point S is determined based on the following considerations:

S is outside the mask Mask_S.

The gray value of S should be as close as possible to one of the thresholds lower_threshold and upper_threshold.

S must be inside the close neighbourhood of the mask Mask_S.

S must be as close to the previous mask Mask_final as possible.

The seed point replacement algorithm takes over the previous algorithm with an additional step to extend the size of adjacency area mask.

Algorithm

1. Find in the 3D volume the slice fulfilling the conditions of being the closest to Mask_final in one hand and including adjacent voxels to Mask_S in the other hand. It must be that this slice does not intersect Mask_S. Let the found slice be called Slice_Adjacent.

2. Extract Mask_Adjacent which is a 2D binary mask corresponding to the adjacent voxels to Mask_S that are included in Slice_Adjacent.

3. Extend the size of Mask_Adjacent. The extension can be achieved by a morphological dilation with a square shape structural element of size 3.

4. In Mask_Adjacent, find the voxel S1 having the closest gray value to lower_threshold. Let distance1 be the gray value distance between S1 and lower_threshold.

5. In Mask_Adjacent, find the voxel S2 having the closest gray value to upper_threshold. Let distance2 be the gray value distance between S2 and upper_threshold.

6. The final seed point S (the output of the current algorithm) is S1 if distance1 is lower than distance2 and S is given by S2 otherwise.

Having described in detail preferred embodiments of the current invention, it will now be apparent to those skilled in the art that numerous modifications can be made therein without departing from the scope of the invention as defined in the appending claims.

Although the invention has been explained with regard to vessel segmentation, the method is also applicable to segmentation of other types of structures.

The invention claimed is:

1. A method of segmenting an anatomical structure in a volume represented by a 3D digital representation, the method comprising the steps of:

applying a region growing algorithm to the volume starting from a seed point to generate a final mask;

evaluating the final mask to identify one or more regions including unconnected structures;

when a region of the one or more regions including unconnected structures is found, identifying a new seed point in the region;

applying the region growing algorithm to the new seed point resulting in a seed mask; and when the seed mask intersects with the final mask, creating a segmentation mask as a combination of the seed mask and the final mask and displaying the segmentation mask of the anatomical structure, otherwise, applying a locally adaptive region growing iteration including iteratively performing the region growing algorithm to a next seed point to generate a new mask until the new mask intersects the final mask; wherein the locally adaptive region growing iteration includes:

determining a first gray value distance between the next seed point and a low threshold value used to generate the seed mask and a second gray value distance between the next seed point and a high threshold value used to generate the seed mask;

determining a minimum distance between the first and second gray value distances;

when the minimum distance is lower than a preset threshold, enlarging a range between the low and the high threshold values so as to encompass the next seed point by replacing the low threshold value by a minimum of the low threshold value and the gray value of the next seed point and by replacing the high threshold value by a maximum of the high threshold and the gray value of the next seed point, otherwise replacing the next seed point by the new seed point; and applying the region growing algorithm to the volume starting from the new seed point to generate the new mask.

2. The method according to claim 1, wherein the next seed point is automatically determined based on the following steps:

finding in the volume a slice region which fulfils properties including:

the slice region does not intersect the seed mask;

the slice region is adjacent to the seed mask; and the slice region is as close as possible to the final mask; and finding in the slice region, a next seed point such that a gray value of the next seed point is closest to one of a low threshold value and a high threshold value used to generate the seed mask.

3. The method according to claim 2, wherein the new seed point is automatically determined by the following steps:
   applying a morphological dilation to the slice region resulting in a dilated region; and
   finding, in the dilated region, the new seed point such that a gray value of the new seed point is closest to one of low threshold and high threshold values used to generate the seed mask.

4. The method according to claim 1, wherein a number of pixels within the new mask resulting from one iteration is compared with a number of pixels in a mask generated in a previous iteration and wherein excessive growth is detected if a ratio of the number of pixels from the one iteration to the number of pixels in the previous iteration exceeds a predetermined number.

* * * * *